United States Patent [19]

Gairns et al.

[11] Patent Number: 5,395,969
[45] Date of Patent: Mar. 7, 1995

[54] CHEMICAL COMPOUNDS

[75] Inventors: Raymond S. Gairns, Whitefield; Anthony A. Watson, Cheetham, both of England

[73] Assignee: Zeneca Limited, London, England

[21] Appl. No.: 95,996

[22] Filed: Jul. 23, 1993

Related U.S. Application Data

[63] Continuation of Ser. No. 802,615, Dec. 5, 1991, abandoned.

[30] Foreign Application Priority Data

Dec. 13, 1990 [GB] United Kingdom ............... 9027031

[51] Int. Cl.⁶ .................. C07C 211/48; C07C 211/58
[52] U.S. Cl. ...................................... 564/315; 548/440
[58] Field of Search ............................. 564/315

[56] References Cited

FOREIGN PATENT DOCUMENTS 57-179856 11/1982 Japan .

OTHER PUBLICATIONS

Bahner, J. Med. Chem, 12 722 (1969).

*Primary Examiner*—Robert Gerstl
*Attorney, Agent, or Firm*—Cushman Darby & Cushman

[57] ABSTRACT

A compound suitable for use as a charge transport compound in organic photoconductors or as a charge control agent in electrophotographic toners. The compound, in the neutral form, is of the Formula (1):

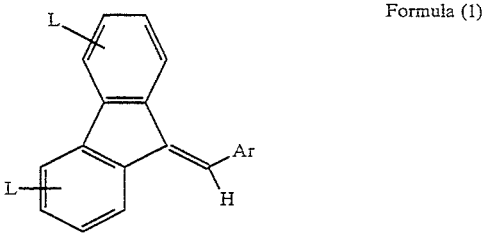

Formula (1)

wherein:
Ar is of formula (a), (b) or (c)

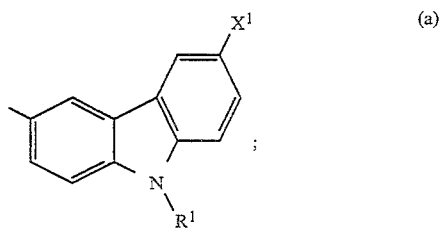

(a)

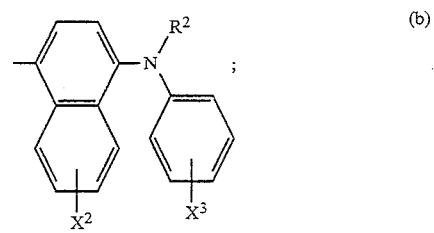

(b)

or

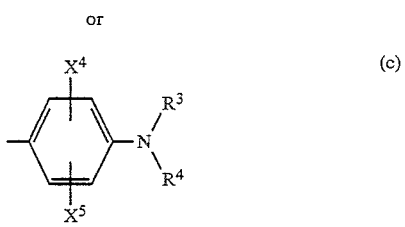

(c)

each L independently is H, $C_{1-4}$-alkyl or halo;
$R^1$, $R^3$ and $R^4$ are each independently alkyl, substituted alkyl, aryl, substituted aryl, aralkyl, substituted aralkyl, cycloalkyl or allyl;
$R^2$ is an alkyl, aralkyl, cycloalkyl, allyl or aryl group which is unsubstituted or substituted by a group defined by $X^4$; and
$X^1$, $X^2$, $X^3$, $X^4$ & $X^5$ are each independently H or a group capable of stabilising a positive charge on the adjacent carbon atom.

4 Claims, No Drawings

CHEMICAL COMPOUNDS

This is a continuation of application No. 07/802,615, filed on Dec. 5, 1991, now abandoned.

This invention relates to a new chemical compound which is useful as a charge transport compound (CTC) in a photoconductor device or as positive-charging, charge control agent in a reprographic toner.

According to the present invention there is provided a compound which, in the neutral form, is of the Formula (1):

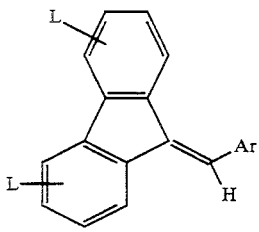

Formula (1)

wherein:
AR is of formula (a), (b) or (c)

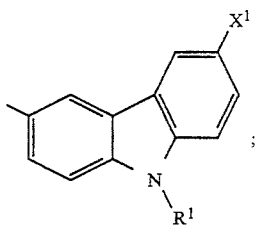
(a)

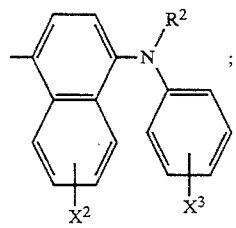
(b)

or

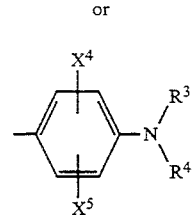
(c)

each L independently is H, $C_{1-4}$-alkyl or halo;
$R^1$, $R^3$ and $R^4$ are each independently alkyl, substituted alkyl, aryl, substituted aryl, aralkyl, substituted aralkyl, cycloalkyl or allyl;
$R^2$ is an alkyl, aralkyl, cycloalkyl, allyl or aryl group which is unsubstituted or substituted by a group defined by $X^4$; and
$X^1$, $X^2$, $X^3$, $X^4$ and $X^5$ are each independently H or a group capable of stabilising a positive charge on the adjacent carbon atom.

Each L independently is preferably methyl, chloro or especially H.

When any of $R^1$, $R^2$, $R^3$ and $R^4$ are optionally substituted aralkyl they preferably have less than 12 carbon atoms, more preferably less than 8 carbon atoms.

As examples of optionally substituted aralkyl groups represented by $R^1$, $R^2$, $R^3$ and $R^4$ there may be mentioned benzyl, —$CH_2$-naphthyl and substituted derivatives thereof.

When any of $R^1$, $R^2$, $R^3$ and $R^4$ is optionally substituted aryl it preferably has less than seven carbon atoms, and more preferably is optionally substituted phenyl, especially unsubstituted phenyl.

As examples of optionally substituted aryl groups represented by any of $R^1$, $R^2$, $R^3$ and $R^4$ there may be mentioned phenyl, 3-methylphenyl, 4-methoxyphenyl, 3-aminophenyl and 4-thiomethylphenyl.

When any of $R^1$, $R^2$, $R^3$ and $R^4$ is optionally substituted alkyl it is preferably optionally substituted $C_{1-4}$-alkyl. However, it is preferred that $R^2$ is benzyl or $C_{1-4}$-alkyl and at least one, or preferably both of $R^3$ and $R^4$ are independently selected from $C_{1-4}$-alkyl. The preferences for $R^2$, $R^3$ and $R^4$ being $C_{1-4}$-alkyl arises from the finding that this confers good surface potential, low dark decay and low residual potential to an OPC containing a compound of Formula (1) in which $R^2$, $R^3$ or $R^4$ is $C_{1-4}$-alkyl.

As examples of optionally substituted alkyl groups represented by any of $R^1$, $R^2$, $R^3$ and $R^4$ there may be mentioned methyl, ethyl, propyl, methoxymethyl, —$CH_2$—S—$CH_3$ and —$CH_2CH_2N(CH_3)_2$.

The optional substituents present on $R^1$, $R^3$ and $R^4$ are preferably independently selected from methyl, methoxy, methylthio and amino.

$R^1$, $R^2$, $R^3$ and $R^4$ and are preferably each independently methyl or ethyl.

It is preferred that Ar is of formula (b) or (c).

The term "group capable of stabilising a positive charge on the adjacent carbon atom" is hereinafter abbreviated as an "EDG group". An EDG group is defined as a group which, if it were attached to a benzene ring, would be ortho or para directing towards electrophilic substitution; such groups include electron donating groups, and groups which are not electron donating but by virtue of a free electron pair are ortho or para directing, e.g. alkyl, alkoxy, hydroxy, amino, acylamino, substituted amino, ester and halo groups.

The preferred EDG groups are selected from $C_{1-4}$-alkyl, especially methyl; $C_{1-4}$-alkoxy, especially methoxy; hydroxy; —S—($C_{1-4}$alkyl), especially —S—$CH_3$;

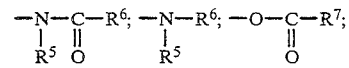

chloro and bromo;
wherein $R^5$ and $R^6$ are each independently H or $C_{1-4}$-alkyl, and $R^7$ is $C_{1-4}$-alkyl.

As specific examples of EDG groups there may be mentioned methyl, methoxy, hydroxy, acetamido, amino, dimethylamino, acetoate, chloro and bromo.

$X^1$, $X^2$, $X^4$ and $X^5$ are each preferably H so as to confer reasonable solubility and low residual potential to the compound of Formula (1).

$R^2$ is preferably $C_{1-4}$-alkyl, especially methyl or ethyl.

In a particularly preferred compound of Formula (1) L is H; $R^1$, $R^3$ and $R^4$ are each independently alkyl; $R^2$ is an alkyl group; and $X^1$, $X^2$, $X^3$, $X^4$ and $X^5$ are H.

The compound of Formula (1) is especially useful as charge transport compound (CTC) in an organic photoconductor (OPC) such as is used in electrophotographic copiers and printers. Such an OPC generally comprises an electrically conducting substrate carrying a charge generation layer (CGL) and a charge transport layer (CTL) which may be separate or combined in a single phase. Such an OPC may be prepared using methods known in the art.

The immediate substrate is an electrically conducting material, which may be provided (a) by a rigid metal, e.g. aluminium, support, preferably in the form of a drum; or (b) by a composite material, in the form of a drum or a continuous belt, comprising an insulating support such as a sheet or film of polymeric material, e.g. a polyester, coated with a thin film of an electrically conducting material, e.g. aluminium.

The CGL may comprise charge generating compound (CGC) alone preferably in the form of a layer deposited on the substrate, or the CGC may be dispersed in a resin and formed into a layer on the substrate. Examples of suitable resins for use in the CGL are polycarbonate, polyester, polystyrene, polyurethane, epoxy, acrylic, styrene-acrylic, melamine, polyvinylbutyral and silicone resins. Where the resin (e.g. a polycarbonate) does not have good adhesive properties with respect to the substrate, adhesion between the resin and the substrate may be improved by the use of an adhesive resin. A specific example of a suitable resin for use in the CGL is LEXAN 141 Natural (General Electric Plastics, Europe). A suitable adhesive resin for bonding the CGL to the substrate is VMCA (Union Carbide).

Suitable CGC for use in the CGL include dyes and especially pigments of various chemical types, for example azo, squaraine, thiapyrilium, phthalocyanine and polycyclic aromatic carbonyl compounds. Preferred CGCs are selected from the group consisting of X-form metal free phthalocyanines and titanyl phthalocyanines in the alpha or gamma form.

The CTL preferably comprises a layer of a resin containing the CGC of Formula (1) and preferably has a thickness from 1.0 micrometer to 50 micrometers and more preferably from 5.0 micrometers to 30 micrometers. Examples of suitable resins for use in the CTL include one or more of polycarbonate, polyester, polystyrene, polyurethane, epoxy, acrylic, styrene-acrylic, melamine and silicone resins. A preferred resin for use in CTL is LEXAN 141.

The new compound of the present invention is also suitable as a colourless charge control agent (CCA) for use in an electrophotographic toner, especially a positive charging toner. The CCA is especially valuable in two component systems (toner+carrier) but is also suitable for a one-component toner or liquid toner.

The invention is illustrated by the following Examples in which all parts and percentages are by weight unless otherwise stated.

EXAMPLE 1

Preparation of the Compound of Formula (1) wherein Ar is 4-(N,N-diethylamino)phenyl and L is H

Stage 1—Preparation of 9-bromofluorene

A mixture of fluorene (MW 166, 0.36M, 59.76 g), N-bromosuccinimide (MW 178, 0.36M, 64.1 g), benzoyl peroxide (MW 242, 0.0036M, 0.87 g) and carbon tetrachloride (360 ml) was stirred at reflux for 3 hours. After cooling to room temperature and screening, the filtrates were evaporated under reduced pressure to yield a dark oil, which after crystallisation from methanol gave 46.1 g of the title product (55% yield) as a yellow solid, m.p. 102°–104° C.

$^1$H nmr (250 MH$_z$, CDCl$_3$ solvent) showed peaks at 5.96 (1H, S) and 7.24–7.8 (8H, m).

The mass spectrum showed peaks at 245 (M+), 165 (100%) and 139.

Stage 2—Preparation of 9-(diethylphosphityl)fluorene

A mixture of 9-bromofluorene (MW 245, 0.197M, 48.27 g) and triethylphosphite (MW 166, 0.217M, 36 g) was stirred at 150° C. until evolution of ethyl bromide ceased (approximately 30 minutes). The mixture was cooled to room temperature to give an orange liquid which was not subjected to further purification. Yield 58.4 g (98%) C$_{17}$H$_{19}$O$_3$P=MW 302.

Stage 3—Preparation of the Compound of Formula (1) wherein Ar is 4-(N,N-diethylamino)phenyl and L is H A mixture of 4-(N,N-diethylamino)benzaldehyde (MW 177, 0.02M, 3.54 g), the product of Example 2 (MW 302, 0.02M, 6.04 g), sodium hydride (0.6 g, 80%, 0.02M) and dimethyl sufoxide (dried, 30 ml) were stirred at 100° C. for 3 hours. The mixture was cooled to room temperature, poured into water (150 ml) and extracted with dichloromethane (2×100 ml). The combined extracts were dried over MgSO$_4$ and purified by flash chromatography (MERCK 60H Art 7736) eluting with petrol (40°–60°)/dichloromethane to give 1.0 g of the title product as an orange liquid (15% yield). C$_{24}$H$_{23}$N=MW 325.

$^1$H nmr (250 MH$_z$, CDCl$_3$ solvent) showed peaks at 1.22 (6H, t, J=8 Hz), 3.43 (4H, q, J=8 Hz) and 6.65–8.1 (13H, m).

The mass spectrum showed peaks at 325 (M+, 100%), 310, 281 and 252.

Combustion of a sample of title product showed 88.8% Carbon (Theory 88.6%); 6.9% Hydrogen (Theory 7.1%) and 4.3% Nitrogen (Theory 4.3%).

EXAMPLE 2

Preparation of the Compound of Formula (1) wherein Ar is 4-(N-methyl-N-phenylamino)phenyl and L is H The procedure of Example 1, stage 3 was followed except that in place of 4-(N,N-diethylamino)benzaldehyde there was used 4-(N-methyl-N-phenylamino)benzaldehyde (MW 211, 0.02M, 4.22 g) to give 0.8 g of the title product as an orange liquid (11% yield). C$_{27}$H$_{21}$N=MW 359.

$^1$H nmr (250 MH$_z$, CDCl$_3$ solvent) showed peaks at 3.4 (3H, S) and 6.95–7.95 (18H, m).

The mass spectrum showed peaks at 359 (M+, 100%), 252 and 179.

EXAMPLE 3

Preparation of the Compound of Formula (1) wherein Ar is 4-(N-methyl-N-phenylamino)naphthyl and L is H The procedure of Example 1, stage 3 was followed on the 0.01M scale except that in place of 4-(N,N-diethylamino)benzaldehyde there was used 1-formyl-4-(N-methyl-N-phenylamino)naphthalene (MW 261, 0.01M, 2.61 g). 0.85 g of the title product was obtained, in the form of an orange solid, m.p. 87°–88° C., (31% yield). C$_{31}$H$_{23}$N=MW 409.

¹H nmr (250 MH$_z$, CDCl$_3$ solvent) showed peaks at 3.48 (3H, S) and 6.62–8.0 (20H, m).

The mass spectrum showed peaks at 409 (M+, 100%), 205 and 196.

EXAMPLE 4

Preparation of the Compound of Formula (1) wherein Ar is 4-(N,N-diphenylamino)phenyl and L is H

Stage 1

Phosphorus oxychloride (MW 153, 0.129M, 19.7 g) was added dropwise to dimethylformamide ("DMF") (MW 73, 0.774M, 56.5 g) maintaining the temperature at <10° C. with external cooling. Triphenylamine (MW 245, 0.129M, 31.5 g) was added and the reaction mixture stirred at 100° C. for 1 hour. After cooling to room temperature and pouring into water (500 ml), the suspension was neutralised to pH 6 with saturated sodium acetate solution. The suspension was filtered off and washed with water, then redissolved in dichloromethane and dried over MgSO$_4$ before screening through Silica gel (MERCK 60H Art 7736) and solvent removed under reduced pressure to give 27.5 g of 4-(N,N-diphenylamino) benzaldehyde (78% yield) as a yellow solid, m.p. 132°–133° C.

¹H nmr (250 MH$_z$, CDCl$_3$ solvent) showed peaks at 6.95–7.7 (14H, m) and 9.8 (1H, S).

The mass spectrum showed peaks at 273 (M+, 100%) and 244.

Microanalysis of a sample showed the presence of 83.3% Carbon (Theory 83.5%), 5.5% Hydrogen (Theory 5.5%) and 5.0% Nitrogen (Theory 5.1%).

Stage 2

The procedure of Example 1, stage 3 was followed on the 0.05M scale except that in place of 4-(N,N-diethylamino)benzaldehyde there was used 4-(N,N-diphenylamino)benzaldehyde (MW 273, 0.005M, 1.37 g). The title product was obtained as a yellow solid, m.p. 77°–79° C., in a yield of 0.66 g (31% yield).

¹H nmr (250 MH$_z$, CDCl$_3$ solvent) showed peaks at 6.95–7.9 (23H, m).

The mass spectrum showed peaks at 421 (M+, 100%) and 211.

EXAMPLE 5

Preparation of the Compound of Formula (1) Wherein Ar is N-ethylcarbazol-3-yl and L is H The procedure of Example 4 was followed except that in place of 4-(N,N-diphenylamino)benzaldehyde there was used 3-formyl-N-ethylcarbazole (MW 223, 0.005M, 1.12 g), to give 0.5 g (27% yield) of the title product as a yellow solid, m.p. 171°–173° C.

¹H nmr (250 MH$_z$, CDCl$_3$ solvent) showed peaks at 1.5 (3H, t, J=8 Hz), 4.4 (2H, q, J=8 Hz) and 6.95–8.4 (16H, m).

The mass spectrum showed peaks at 371 (M+, 100%), 356 and 341.

EXAMPLE 6

Preparation of the Compound of Formula (1) Wherein Ar is 4-(N,N-diphenylamino)naphth-1-yl and L is H

Stage 1

Preparation of 1-formyl-4-(N,N-diphenylamino)naphthalene

The method of Example 4, Stage 1, was followed except that there was used 4.7 g of POCl$_3$, 13.6 g of DMF, and in place of triphenylamine there was used N,N-diphenyl-1-naphthylamine (MW 295, 0.031M, 9.2 g) to give 4 g (40% yield) of 1-formyl-4-(N,N-diphenylamino) naphthalene as a yellow solid, m.p. 107°–110° C.

¹H nmr (250 MH$_z$, CDCl$_3$ solvent) showed peaks at 6.82–7.94 (16H, m) and 9.77 (1H, S).

The mass spectrum showed peaks at 323 (M+, 100%), 294 and 217.

Stage 2

The procedure of Example 4, Stage 2, was followed except that in place of 4-(N,N-diphenylamino)benzaldehyde there was used 1-formyl-4-(N,N-diphenylamino)-naphthalene (MW 323, 0.005M, 1.62 g), to give 0.8 g (34% yield) of the title product as a yellow solid, m.p. 106°–108° C.

¹H nmr (250 MH$_z$, CDCl$_3$ solvent) showed peaks at 6.95–8.0 (25H, m).

The mass spectrum showed peaks at 471 (M+, 100%), 252,236 and 217.

EXAMPLE 7

Preparation of the Compound of Formula (1) Wherein Ar is 4-(N-benzyl-N-phenylamino)naphth-1-yl and L is H

Stage 1—Preparation of 1-(N-benzyl-N-phenylamino)naphthalene

Benzyl bromide (0.15M) was added to a stirred mixture of 1-phenylaminonaphthalene (0.1M) and KOH (0.15M) in N-methyl pyrrolidone (70 cm$^3$) at 120° C. After 2 hours further stirring the mixture was poured in to water, the precipitate filtered off, washed and recrystallised from methanol to give 20 g (65% yield) of a white solid mp 120°–123° C.

Stage 2—Preparation of 1-formyl-4(N-benzyl-N-phenylamino)napthalene

The method of Example 4, stage 1 was followed except that in place of triphenylamine there was used 1-(N-benzyl-N-phenylamino) naphthalene.

The product resulted in 56% yield as a yellow liquid having ¹H NMR peaks at (delta, 250 MH$_z$, CDCl$_3$) 5.04 (2H, S), 6.55–8.0 (16H, m) and 9.7 (1H, S).

Stage 3

The procedure of Example 1, stage 3 was followed on the 0.01M scale except that in place of 4-(N,N-diethylamino)benzaldehyde there was used 1-formyl-4-(N-benzyl-N-phenylamino)napthalene to give the title product (0.27 g, 6% yield) as an orange solid, mpt 88°–90° C., ¹H NMR (delta, 400 MH$_3$, CDCl$_3$) 5.2 (2H, S) and 6.62–8.0 (25H, M).

EXAMPLE 8

Preparation of the Compound of Formula (1) Wherein Ar is 4-(N-phenyl-N-ethylamino)naphth-1-yl and L is H

Stage 1

A mixture of ethyl iodide (0.1M), 1-phenylaminonaphthalene (0.05M), KOH (0.1M) and copper bronze (1 g) was stirred for 3½ hours in N-methylpyrrolidone (20 cm$^3$) at 120° C. under an atmosphere of nitrogen. The mixture was cooled, poured into water (2 liters) and extracted with CH$_2$Cl$_2$ (3×300 cm$^3$). The combined extracts were washed with water, dried over MgSO$_4$ and the CH$_2$Cl$_2$ solvent removed in vacuo to give 229 g (98% yield) of 1-(N-phenyl-N-ethylamino)naphthalene as a yellow liquid.

Stage 2

The method of Example 1, stage 1 was followed on the 0.05M scale except that in place of triphenylamine there was used 1-(N-phenyl-N-ethylamino)naphthalene, to give 1-formyl-4-(N-phenyl-N-ethylamino)naphthalene (11 g, 80% yield) as a yellow liquid, $^1$NMR (delta, 250 MH$_3$, CDCl$_3$) showed peaks at 1.32 (3H, t), 3.9 (2H, q), 6.5–7.96 (11H, m) and 9.73 (1H, S).

Stage 3

The procedure of Example 1, stage 3 was followed on the 0.01M scale except that in place of 4-(N,N-diethylamino)benzaldehyde there was used 1-formyl-4-(N-phenyl-N-ethylamino)naphthalene to give the title product (0.65 g, 15% yield) as a yellow solid, mpt 85°–87° C. $^1$H NMR (delta, 250 MHz, CDCl$_3$) showed peaks at 1.32 (3H, t), 3.88 (2H, q) and 6.58–8.03 (20H, M).

EXAMPLES 9 to 16

Metal-free phthalocyanine (0.45 g) and polyester resin (VITEL PE200 from Goodyear) (0.45 g) were added to a bottle containing 3 mm glass beads (25 g) and 4:1 dichloromethane:toluene (DCM/T) (10 ml) and shaken for 1 h on a Red Devil paint shaker. The dispersion was diluted with 4:1 DCM/T (10 ml), coated onto 100 micron aluminised polyester film (MELINEX from ICI), using a 6 micron (wet thickness) wire-wound bar and dried to form a charge generation layer (CGL). The polyester film had been precoated with a 2% wt/v solution of an adhesive polymer in 9:1 tetrahydrofuran:toluene using a 6 micron (wet thickness) wire-wound bar. The CGL was overcoated with an 8.6% wt/wt solution of a charge transport compound (CTC) as identified in Table 1 in a 9.4% wt/v solution of polyester resin (VITEL PE200) in DCM/T (9:1) using a 150 micron (wet thickness) wire-wound bar, dried at 70° C. for 3 hours to form an OPC comprising a CGL and a CTL.

Each OPC was tested using a Kawaguchi Electric Works Model SP428 Electrostatic Paper Analyser, in the dynamic mode. The following properties were measured:

$V_1$ Surface potential (volt) of sample after 10 seconds charging with a 6 kV corona.

$V_2$ Surface potential (volt) after 5 seconds in dark conditions.

DD Dark decay (%) given by the expression:

$$DD = \frac{V_1 - V_2}{V_1} \times 100$$

S Sensitivity (lux sec): the product of the light intensity (hue) and the time (sec) taken to reduce the surface potential by 50%.

$V_r$ Residual Potential (volt) remaining on surface after illumination for 10 sec.

The results are set out in Table 1:

TABLE 1

| Example | CTC | $V_1$ (volts) | $V_2$ (volts) | DD (%) | S (lux sec) | $V_r$ (volt) |
|---|---|---|---|---|---|---|
| 9 | Ex 1 | 1160 | 990 | 15 | 1.3 | 20 |
| 10 | Ex 2 | 940 | 780 | 17 | 1.1 | 20 |
| 11 | Ex 3 | 920 | 750 | 19 | 0.95 | 45 |
| 12 | Ex 4 | 440 | 250 | 43 | 0.6 | 15 |
| 13 | Ex 5 | 800 | 590 | 26 | 1.3 | 170 |
| 14 | Ex 6 | 460 | 300 | 35 | 0.7 | 40 |
| 15 | Ex 7 | 1020 | 680 | 33 | 1.2 | 110 |
| 16 | Ex 8 | 640 | 460 | 28 | 0.7 | 30 |

We claim:

1. A compound which, in the neutral form, is of the Formula (1):

Formula (1)

wherein:
Ar is of formula (b) or (c)

(b)

or (c)

each L independently is H, $C_{1-4}$-alkyl or halo;
$R^3$ and $R^4$ are each independently 3-methylphenyl, 4-methoxyphenyl, 3-aminophenyl, 4-thiomethylphenyl, methoxymethyl, —CH$_2$—S—CH$_3$, —CH$_2$CH$_2$N(CH$_3$)$_2$ or —CH$_2$-naphthyl;
$R^2$ is $C_{1-4}$-alkyl, benzyl, methoxymethyl, —CH$_2$—S—CH$_3$, or —CH$_2$CH$_2$N(CH$_3$)$_2$; and
$X^2$, $X^3$, $X^4$, and $X^5$ are each independently H, $C_{1-4}$-alkyl, $C_{1-4}$-alkoxy, hydroxy, —S—($C_{1-4}$-alkyl), —NR$^5$—CO—R$^6$, —NR$^5$—R$^6$, —O—CO—R$^7$, chloro or bromo wherein R$^5$ and R$^6$ are each independently H or $C_{1-4}$-alkyl and R$^7$ is $C_{1-4}$-alkyl.

2. A compound according to claim 1 wherein $R^2$ is benzyl or $C_{1-4}$-alkyl.

3. A compound according to claim 1 wherein $R^2$ is methyl or ethyl.

4. A compound according to claim 1 wherein:
L is H;
$R^2$ is $C_{1-4}$-alkyl; and $X^2$, $X^3$, $X^4$ and $X^5$ are H.

* * * * *